United States Patent [19]

Pfirmann et al.

[11] Patent Number: 5,430,173
[45] Date of Patent: Jul. 4, 1995

[54] PROCESS FOR PREPARING ALKYL 3-HYDROXY-2, 4, 5-TRIFLUOROBENZOATES AND/OR ALKYL 3-ALKOXY-2, 4, 5-TRIFLUOROBENZOATES

[75] Inventors: Ralf Pfirmann, Griesheim; Theodor Papenfuhs, Frankfurt am Main, both of Germany

[73] Assignee: Hoechst Aktiengesellschaft, Frankfurt, Germany

[21] Appl. No.: 306,763

[22] Filed: Sep. 15, 1994

[30] Foreign Application Priority Data

Sep. 18, 1993 [DE] Germany .................. 43 31 799.5

[51] Int. Cl.⁶ .............................................. C07C 69/76
[52] U.S. Cl. ........................................................ 560/65
[58] Field of Search .......................................... 560/65

[56] References Cited

U.S. PATENT DOCUMENTS 3,867,427  2/1975  Priddy ..................... 560/65
4,513,146  4/1985  Thompson ............... 560/231

Primary Examiner—Paul J. Killos
Attorney, Agent, or Firm—Connolly & Hutz

[57] ABSTRACT

The present invention relates to a process for preparing alkyl 3-hydroxy-2,4,5-trifluorobenzoate and/or alkyl 3-alkoxy-2,4,5-trifluorobenzoate by reacting 3-hydroxy-2,4,5-trifluorobenzoic acid with a dialkyl carbonate at 80° to 200° C.

32 Claims, No Drawings

PROCESS FOR PREPARING ALKYL 3-HYDROXY-2, 4, 5-TRIFLUOROBENZOATES AND/OR ALKYL 3-ALKOXY-2, 4, 5-TRIFLUOROBENZOATES

The present invention relates to an advantageous process for preparing alkyl 3-hydroxy-2,4,5-trifluorobenzoate and/or alkyl 3-alkoxy-2,4,5-trifluorobenzoate. The abovementioned materials, in particular methyl 3-hydroxy-2,4,5-trifluorobenzoate and methyl 3-methoxy-2,4,5-trifluorobenzoate, and also 3-methoxy-2,4,5-trifluorobenzoic acid preparable by hydrolysis of alkyl 3-methoxy-2,4,5-trifluorobenzoate are important prerequisites for preparing bactericides from the series of fluoroquinolone-carboxylic acids.

The conversion of 3-alkoxy-2,4,5-trifluorobenzoic acids into bactericides can be carried out via several steps using methods known from the literature (EOS 241,206 and EOS 230,295). Methyl 3-methoxy-2,4,5-trifluorobenzoate can also be used for synthesizing bactericides. Its conversion into other precursors required for this synthesis can be effected by the method of U.S. Pat. No. 5,047,538. To prepare specific 2,4,5-trifluorobenzoic acids substituted in the 3-position in particular those containing arylated alkyl groups, which are used as precursors for preparing bactericides, the corresponding alkyl 3-hydroxy-2,4,5-trifluorobenzoate, in particular methyl 3-hydroxy-2,4,5-trifluorobenzoate (JP 04,230,344), is required.

3-Methoxy-2,4,5-trifluorobenzoic acid can be prepared by methylation of 3-hydroxy-2,4,5-trifluorobenzoic acid with dimethyl sulfate (JP 03,232,838, JP 01,268,662) or by decarboxylation of 3,5,6-trifluoro-4-methoxyphthalic acid (JP 03,279,348) with bases in dipolar aprotic solvents. Although alkylation (methylation) with a dialkyl sulfate (dimethyl sulfate) proceeds smoothly for the most part, the extremely high toxicity and carcinogenity of dialkyl sulfates (dimethyl sulfate) makes it highly problematical to carry out this reaction in industry. Moreover, owing to the high reactivity of dialkyl sulfate (dimethyl sulfate), alkylation (methylation) of 3-hydroxy-2,4,5-trifluorobenzoic acid proceeds in a comparably uncontrolled manner, as a result of which the reaction cannot, as would be desirable, be carried out selectively.

Although the decarboxylation of 3,5,6-trifluoro-4-methoxyphthalic acid likewise proceeds smoothly, its selectivity cannot be controlled in such a manner that exclusively the desired 3-methoxy compound is formed. It always leads to the formation of the undesirable by-product 4-methoxy-2,3,5-trifluorobenzoic acid, which is difficult to separate off and is subsequently carried over in the further synthesis of the active compound and can possibly lead to toxic impurities in the anti-bacterial substance.

Methyl 3-methoxy-2,4,5-trifluorobenzoate can be prepared by complete methylation of 3-hydroxy-2,4,5-trifluorobenzoic acid with dimethyl sulfate using standard methods or by esterification of 3-methoxy-2,4,5,-trifluorobenzoic acid with alcohols using acid catalysts.

The object of the present invention is to provide a simple process for preparing alkylation products of 3-hydroxy-2,4,5-trifluorobenzoic acid which the desired products not only in high yield and purity but also makes it unnecessary to use highly toxic substances and avoids the formation of undesirable waste, water which pollutes the environment.

This object is achieved by a process for preparing alkyl 3-hydroxy-2,4,5-trifluorobenzoate and/or alkyl 3-alkoxy-2,4,5-trifluorobenzoate. It comprises reacting 3-hydroxy-2,4,5-trifluorobenzoic acid with a dialkyl carbonate at 80° to 200° C. in the absence or presence of at least one catalyst.

The process according to the invention provides compounds alkylated on the carboxyl group and/or hydroxyl group. The starting material used for the synthesis is 3-hydroxy-2,4,5-trifluorobenzoic acid which in turn is a precursor for preparing antibacteriol substances and can be prepared by known methods from tetrafluorophthalic acid by exchange of a fluorine atom for a hydroxyl group, followed by decarboxylation of the corresponding hydroxy compound. In contrast to dialkyl sulfates, in particular dimethyl sulfate, dialkyl carbonates, in particular dimethyl carbonates, have substantially lower toxicity, which may be due to the fact that dialkyl carbonates and dimethyl carbonate hardly exhibit a methylating effect under standard conditions, i.e., at standard pressure and standard temperature. A comparison of the toxicological data of dimethyl carbonate as an example of a dialkyl carbonate and dimethyl sulfate as a representative of a dialkyl sulfate shows serious differences. Thus, $LD_{50}$ of dimethyl carbonate (rat, orally) is 12,800 mg/kg of body weight, but the corresponding value for dimethyl sulfate is 440 mg/kg of body weight and thus lower by a factor of almost 30, i.e., the toxicity is correspondingly higher. The corresponding $LD_{50}$ of dimethyl carbonate for subcutaneous injection is 8500 mg/kg of body weight, but that of dimethyl sulfate is only 30 mg/kg of body weight.

If dimethyl carbonate is inhaled by a rat, concentrations of up to 1000 ppm do not give any poisoning effects over a period of 6 hours; upon increasing the dose to 5000 ppm, the effects become visible but they rapidly subside in a neutral atmosphere. In contrast, dimethyl sulfate already causes death in a concentration of only 30 ppm within 4 hours. Moreover, dimethyl sulfate exhibits teratogenic, mutagenic and carcinogenic effects. In contrast, dimethyl carbonate is as yet not known to have any chronic effects.

A further significant difference of the use of dialkyl carbonates on the one hand and dialkyl sulfates on the other is that the reaction with dialkyl carbonates results in the formation of alcohols and carbon dioxide as waste products, while in the reaction with dialkyl sulfates only one alkyl group is utilized for alkylation and water-soluble alkyl sulfates are formed as waste products. Since the reactions with dialkyl sulfates are usually carried out in the presence of water, they always lead to waste water which is correspondingly strongly polluted with alkyl sulfates.

A particular advantage of the process according to the invention is that the reaction of 3-hydroxy-2,4,5-trifluorobenzoic acid with the dialkyl carbonate can be controlled in such a manner that either the corresponding alkyl 3-hydroxy-2,4,5-trifluorobenzoate or the corresponding alkyl 3-alkoxy-2,4,5-trifluorobenzoate is formed. In both cases, the reaction leads to the desired product in each case at high selectivity. However, mixtures of both substances can also be prepared.

Another advantage of the process according to the invention is the fact that the reaction can be carried out in an anhydrous medium under neutral conditions, i.e., without addition of an acid or basic catalyst. Corrosion problems such as are to be expected when using aqueous mineral acids or aqueous bases are not observed. Omitting such acid or basic catalysts greatly simplifies the feasibility of the process.

If the intention is to prepare alkyl 3-hydroxy-2,4,5-trifluorobenzoate, the reaction is carried out at comparably low temperatures but if it is desired to prepare alkyl 3-alkoxy-2,4,5-trifluorobenzoate the reaction is allowed to proceed at higher temperatures.

These two compounds prepared directly by alkylation—alkyl 3-hydroxy-2,4,5-trifluorobenzoate on the one hand and alkyl 3-alkoxy-2,4,5-trifluorobenzoate on the other can be purified in a simple manner by fractional distillation, which is not possible when using 3-hydroxy-2,4,5-trifluorobenzoic acid and in general only possible with great difficulty for 3-alkoxytrifluorobenzoic acids. In this manner, products of very high purity are obtained, which otherwise is not possible without further elaboration.

The alkylation (methylation) result must be considered surprising since the prior art (M. Lissel et al., Kontakte Darmstadt) 1990 (1), 20–23 and references cited there) shows that alkylation of a carboxyl group usually takes place at significantly higher temperatures than alkylation of a phenolic group. Lissel et al. give a temperature difference of 60° C. for the alkylation of phenols and carboxylic acids.

The reaction is in general carried out in a temperature range from 80° to 200° C.

In many cases, it has proven useful to carry out the reaction at 120° to 195° C., in particular 135° to 195° C. If it is desired to prepare alkyl 3-hydroxy-2,4,5-trifluorobenzoate, 3-hydroxy-2,4,5-trifluorobenzoic acid is usually reacted with the dialkyl carbonate at 80° to 165° C. In a number of cases, it has proven favorable to carry out this reaction (monoalkylation) at 120 to 165, in particular at 135° to 160° C.

If the intention is to prepare alkyl 3-alkoxy-2,4,5-trifluorobenzoate, 3-hydroxy-2,4,5-trifluorobenzoic acid is usually reacted at 145° to 200° C. In many cases, it has proven advantageous to carry out this reaction (dialkylation) at 145 to 195, in particular 150° to 190° C., A selection of suitable process conditions also makes it possible to prepare mixtures containing alkyl 3-hydroxy-2,4,5-trifluorobenzoate and alkyl 3-alkoxy-2,4,5-trifluorobenzoate in any desired ratio.

In many cases, in order to ensure a favorable course of the reaction, it is recommended to use a catalyst. A suitable catalyst is a mixture comprising a metal iodide and an alkylation catalyst. A highly suitable alkylation catalyst is 4-dimethylaminopyridine or 4-dimethylaminopyridine fixed on a solid support. Using 4-dimethylaminopyridine makes the reaction according to the invention particularly easy.

It is surprising that despite using catalystic amounts of base (alkylation catalyst), the alcohol resulting from the reaction of the dialkyl carbonate does not give rise to nucleophilic substitution of a fluoroatom in exchange for an alkoxy group.

Suitable metal iodides are potassium iodide, sodium iodide, rubidium iodide or cesium iodide, in particular sodium iodide or potassium iodide, preferably potassium iodide. Mixtures of these iodides can also be used.

In a number of cases, the additional use of a further catalyst (co-catalyst) has proven to be beneficial. Highly suitable co-catalysts are phase transfer catalysts.

Suitable phase transfer catalysts are crown ethers, in particular 18-crown-6 or dibenzo-18-crown-6. Mixtures of phase transfer catalysts can also be used.

The metal iodide is usually used in an amount of 0.1 to 5, in particular 0.25 to 2, mol %, relative to 3-hydroxy-2,4,5-trifluorobenzoic acid.

The phase transfer catalyst (co-catalyst) is used in an amount of 0.1 to 5, in particular 0.25 to 2, mol %, relative to 3-hydroxy-2,4,5-trifluorobenzoic acid.

It has proven useful to use a catalyst containing the metal iodide and the alkylating catalyst in a specific ratio. The catalyst usually contains 1 to 5, in particular 2 to 3, mol of alkylating catalyst per mole of metal iodide.

The reaction can be carried out in the absence of a catalyst, in which case, however, a lower reaction rate has to be accepted.

To carry out the reaction, 1 to 100, in particular 1.5 to 50, preferably 5 to 30, mol of dialkyl carbonate are used per mole of 3-hydroxy-2,4,5-trifluorobenzoic acid. In the case of monoalkylation, smaller amounts of dialkyl carbonate are usually sufficient, while dialkylation usually requires larger amounts of dialkyl carbonate.

Suitable dialkyl carbonates are those containing 1 to 8, in particular 1 to 4, carbon atoms per alkyl group.

Suitable dialkyl carbonates are dimethyl carbonate, diethyl carbonate, di-n-propyl carbonate or di-n-butyl carbonate. Highly suitable dialkyl carbonates are dimethyl carbonate or diethyl carbonate, in particular dimethyl carbonate.

If desired, the process according to the invention can also be carried out in the presence of an inert solvent. The inert solvent used can be an aliphatic hydrocarbon, an aromatic hydrocarbon, a chlorinated aromatic hydrocarbon, a dipolar aprotic solvent or mixtures of these solvents. Examples of aliphatic hydrocarbons include hexane, heptane or octane, examples of aromatic hydrocarbons include toluene or xylene, examples of chlorinated aromatic hydrocarbons include chlorobenzene, dichlorobenzene or chlorotoluene and examples of dipolar aprotic solvents include tetrahydrofuran, sulfolane, dioxane or N,N-dimethylacetamide.

However, the addition of an inert solvent can also be dispensed with.

Using excess dialkyl carbonate used as the solvent makes the process according to the invention particularly easy.

After the reaction is complete, the solvent or the dialkyl carbonate used in excess is usually distilled off, and the product left in the bottom is recrystallized. When using a crude starting material which is difficult to purify, it is particularly advantageous either to prepurify the value product present in the bottom by a simple distillation at the top and then, if desired, dissolve and crystallize (recrystallize) or to carry out the purification in a single step by fractional distillation until the desired degree of purity is reached.

The process according to the invention can be carried out at atmospheric pressure, reduced pressure or superatmospheric pressure, operation at atmospheric pressure or superatmospheric pressure of up to about 1.0, in particular 0.5, MPa being preferred. The reaction is usually carried out at a constant pressure of up to about 0.5 MPa, and the gas (carbon dioxide) formed in this reaction is removed continuously using a pressure-maintaining device.

The examples which follow document the invention without limiting it.

EXPERIMENTAL SECTION

Example 1

19.2 g (0.1 mol) of 3-hydroxy-2,4,5-trifluorobenzoic acid are dissolved in 100 g of dimethyl carbonate with gentle heating, the mixture is transferred to an autoclave lined with PTFE (polytetrafluoroethylene), 0.5 g of potassium iodide and 0.25 g of 4-dimethylaminopyridine are added, the mixture is heated to 150° C. with stirring and allowed to react for 16 hours. After cooling, the autoclave has a residual pressure of 1 MPa.

The solution, which at the beginning of the reaction is yellow-orange, is dark red after the reaction is complete.

Analysis by gas chromatography shows that the reaction mixture contains, apart from dimethyl carbonate, 89% by GC area of methyl 3-hydroxy-2,4,5-trifluorobenzoate and 11% by GC area of methyl 3-methoxy-2,4,5-trifluorobenzoate (identified by GC/MS). Complete removal of dimethyl carbonate using a rotary evaporator gives 20.4 g of a product mixture as a red oil.

Example 2

0.25 g of potassium iodide, 0.5 g of 4-dimethylaminopyridine and 51 g of crude 3-hydroxy-2,4,5-trifluorobenzoic acid (3-hydroxy-2,4,5-trifluorobenzoic acid content 40.3 g, determined by HPLC and corrected for the response factors) are dissolved in 250 g of dimethyl carbonate with stirring, the mixture is transferred to an autoclave lined with PTFE, heated to 145° C. with stirring and allowed to react for 16 hours. It is then cooled and let down. The solution removed from the autoclave is freed from insoluble residue by filtration, and the dimethyl carbonate is distilled off. The resulting mixture contains <1% of methyl 3-methoxy-2,4,5-trifluorobenzoate. Distillation (1 mbar=0.1 kPa) via a splash guard gives 36 g of a pale yellow oil (temperature at the top 107° to 115° C.). This product is stirred with 200 g of hot water. Cooling and separation gives 33.6 g (0.163 mol) of methyl 3-hydroxy-2,4,5-trifluorobenzoate (78% yield; purity by GC/HPLC >99%).

Example 3

38.4 g (0.2 mol) of 3-hydroxy-2,4,5-trifluorobenzoic acid, 1.2 g of potassium iodide and 2 g of dibenzo-18-crown-6 and 20 g (0.22 mol) of dimethyl carbonate are dissolved in 250 g of N,N-dimethylacetamide with stirring, the mixture is transferred to an autoclave lined with PTFE, heated to 110° C. with stirring and allowed to react for 18 hours.

According to GC, the reaction product does not contain any starting material and only <1% of methyl 3-methoxy-2,4,5-trifluorobenzoate. Excess solvent is distilled off through a short Vigreux column, the remaining oily residue is subjected to fractional distillation, and the substance obtained is stirred with 300 g of hot water. This gives 37.6 g (0.183 mol) of methyl 3-hydroxy-2,4,5-trifluorobenzoate. (91% yield; purity by GC >99%).

Example 4

57.6 g (0.3 mol) of 3-hydroxy-2,4,5-trifluorobenzoic acid, 0.75 g of potassium iodide and 1.4 g of 4-dimethylaminopyridine are dissolved in 250 g of dimethyl carbonate with stirring, the mixture is transferred to an autoclave lined with PTFE, heated to 170° C. with stirring and allowed to react for 8 hours (initial nitrogen pressure at 20° C.: 0.2 MPa; final pressure obtained 3.7 MPa). According to GC, the reaction product does not contain any methyl 3-hydroxy-2,4,5-trifluorobenzoate. After removal of the solvent by distillation and fractional distillation of the remaining bottom product, 58.0 g (0.264 mol) of methyl 3-methoxy-2,4,5-trifluorobenzoate distill over at 3 mm Hg (temperature at the top 100° to 102° C.) as a colorless oil (88% yield, purity 95%).

What is claimed is:

1. A process for preparing alkyl 3-hydroxy-2,4,5-trifluorobenzoate or alkyl 3-alkoxy-2,4,5-trifluorobenzoate or mixtures thereof, which comprises reacting 3-hydroxy-2,4,5-trifluorobenzoic acid with a dialkyl carbonate at 80° to 200° C., optionally in the presence of a catalyst.

2. The process as claimed in claim 1, wherein the reaction is carried out at 120° to 195° C.

3. The process as claimed in claim 1, wherein the reaction results in the formation of alkyl 3-hydroxy-2,4,5-trifluorobenzoate and is carried out at 80° to 165° C.

4. The process as claimed in claim 1, wherein the reaction results in the formation of alkyl 3-alkoxy-2,4,5-trifluorobenzoate and is carried out at 145° to 200° C.

5. The process as claimed in claim 1, wherein a catalyst is used which is a mixture comprising a metal iodide and an alkylation catalyst.

6. The process as claimed in claim 5, wherein the alkylation catalyst used is 4-dimethylaminopyridine or 4-dimethylaminopyridine fixed on a solid support.

7. The process as claimed in claim 5, wherein the metal iodide used is potassium iodide, sodium iodide, rubidium iodide or cesium iodide.

8. The process as claimed in claim 1, wherein a phase transfer catalyst is additionally used as co-catalyst.

9. The process as claimed in claim 8, wherein a crown ether is used as phase transfer catalyst.

10. The process as claimed in claim 5, wherein the metal iodide and the phase transfer catalyst are used in an amount of 0.1 to 5 mol-%, relative to 3-hydroxy-2,4,5-trifluorobenzoic acid.

11. The process as claimed in claim 5, wherein the alkylation catalyst is used in an amount of 1 to 5 mol per mole of metal iodide.

12. The process as claimed in claim 1, wherein 1 to 100 mol of dialkyl carbonate are used per mole of 3-hydroxy-2,4,5-trifluorobenzoic acid.

13. The process as claimed in claim 1, wherein a dialkyl carbonate having 1 to 8 carbon atoms per alkyl group is used.

14. The process as claimed in claim 1, wherein dimethyl carbonate, diethyl carbonate, di-n-propyl carbonate or di-n-butyl carbonate is used as the dialkyl carbonate.

15. The process as claimed in claim 1, wherein dimethyl carbonate or diethyl carbonate is used as the dialkyl carbonate.

16. The process as claimed in claim 1, wherein an inert solvent is used.

17. The process as claimed in claim 1, wherein an aliphatic hydrocarbon, an aromatic hydrocarbon, a chlorinated aromatic hydrocarbon, a dipolar aprotic solvent or mixtures of these solvents are used as the inert solvent.

18. The process as claimed in claim 1, wherein hexane, heptane or octane is used as the aliphatic hydrocarbon, toluene or xylene is used as the aromatic hydrocarbon, chlorobenzene, dichlorobenzene or chlorotoluene is used as the chlorinated aromatic hydrocarbon and/or tetrahydrofuran, sulfolane, dioxane or N,N-dimethylacetamide is used as the dipolar aprotic solvent.

19. The process as claimed in claim 1, wherein the reaction is carried out at 135° to 190° C.

20. The process as claimed in claim 3, wherein the reaction is carried out at 120° to 165° C.

21. The process as claimed in claim 3, wherein the reaction is carried out at 135° to 160° C.

22. The process as claimed in claim 4, wherein the reaction is carried out at 145° to 195° C.

23. The process as claimed in claim 4, wherein the reaction is carried out at 150° to 190° C.

24. The process as claimed in claim 5, wherein the alkylation catalyst used is 4-dimethylaminopyridine fixed on a solid support.

25. The process as claimed in claim 5, wherein the metal iodide is potassium iodide.

26. The process as claimed in claim 8, wherein 18-crown-6 or dibenzo-18-crown-6 is used as a phase transfer catalyst.

27. The process as claimed in claim 5, wherein the metal iodide and phase transfer catalyst are used in an amount of from 0.25 to 2 mol % relative to 3-hydroxy-2,4,5-trifluorobenzoic acid.

28. The process as claimed in claim 5, wherein the alkylation catalyst is used in an amount of from 2 to 3 per mol of metal iodide.

29. The process as claimed in claim 1, wherein 1.5 to 50 mol of dialkyl carbonate are used per mol of 3-hydroxy-2,4,5-trifluorobenzoic acid.

30. The process as claimed in claim 1, wherein 5 to 30 mol of dialkyl carbonate are used per mol of 3-hydroxy-2,4,5-trifluorobenzoic acid.

31. The process as claimed in claim 1, wherein a dialkyl carbonate having 1 to 4 carbon atoms per alkyl group is used.

32. The process as claimed in claim 1, wherein dimethylcarbonate is used as the dialkyl carbonate.

* * * * *